(12) United States Patent
Chen et al.

(10) Patent No.: US 10,952,720 B2
(45) Date of Patent: Mar. 23, 2021

(54) ACHILLES TENDON SUTURE APPARATUS AND METHOD OF USING SAME

(71) Applicants: Hua Chen, Beijing (CN); Peifu Tang, Beijing (CN); HEBEI AINENG BIOTECHNOLOGY CO., LTD, Hebei (CN)

(72) Inventors: Hua Chen, Beijing (CN); Peifu Tang, Beijing (CN)

( * ) Notice: Subject to any disclaimer, the term of this patent is extended or adjusted under 35 U.S.C. 154(b) by 21 days.

(21) Appl. No.: 15/317,762

(22) PCT Filed: Jan. 30, 2015

(86) PCT No.: PCT/CN2015/000069
§ 371 (c)(1),
(2) Date: Dec. 9, 2016

(87) PCT Pub. No.: WO2016/119082
PCT Pub. Date: Aug. 4, 2016

(65) Prior Publication Data
US 2018/0036002 A1     Feb. 8, 2018

(51) Int. Cl.
*A61B 17/04*     (2006.01)
*A61B 17/11*     (2006.01)
(Continued)

(52) U.S. Cl.
CPC .... *A61B 17/0482* (2013.01); *A61B 17/00008* (2013.01); *A61B 17/06066* (2013.01);
(Continued)

(58) Field of Classification Search
CPC ............ A61B 17/0482; A61B 17/1146; A61B 17/06066; A61B 17/00008;
(Continued)

(56) References Cited

U.S. PATENT DOCUMENTS

| 6,200,327 | B1 * | 3/2001 | Assal ................. | A61B 17/0469 606/148 |
| 7,615,062 | B2 * | 11/2009 | Deland ..................... | A61F 2/08 606/148 |
| 9,622,741 | B2 * | 4/2017 | Levine ............... | A61B 17/0482 |

FOREIGN PATENT DOCUMENTS

CN        103417252      * 12/2013

* cited by examiner

*Primary Examiner* — Thomas McEvoy
(74) *Attorney, Agent, or Firm* — Yong Chen

(57) ABSTRACT

A tendo calcaneus suturing instrument, comprising: a first support and a second support that are of a U-shaped structure, a distance adjustment device, a first guide sleeve, a second guide sleeve, a first positioning tube, a second positioning tube and a tendo sheath cutter. An outer arm and an inner arm of the first support, and an outer arm and an inner arm of the second support are respectively provided with a first positioning hole, a first guide hole, a second positioning hole and a second guide hole; and the first guide sleeve/the second guide sleeve is fixed by means of the first positioning hole/the second positioning hole and is matched with the first guide hole/the second guide hole. The first positioning tube/the second positioning tube provided with a through hole is arranged in the first guide sleeve/the second positioning sleeve or the tendo sheath cutter is arranged in the first guide sleeve and/or the second guide sleeve in a matching manner. The tendo calcaneus suturing instrument can simplify the surgical procedure, improve the surgical effect and relieve pains of a patient.

9 Claims, 8 Drawing Sheets

(51) Int. Cl.
*A61B 17/06* (2006.01)
*A61B 17/00* (2006.01)
*A61B 17/3209* (2006.01)
*A61B 17/32* (2006.01)

(52) U.S. Cl.
CPC ...... *A61B 17/1146* (2013.01); *A61B 17/3209* (2013.01); *A61B 2017/06071* (2013.01); *A61B 2017/1132* (2013.01); *A61B 2017/320052* (2013.01)

(58) Field of Classification Search
CPC ...... A61B 17/3209; A61B 2017/06071; A61B 2017/1132; A61B 2017/320052
See application file for complete search history.

ACHILLES TENDON SUTURE APPARATUS AND METHOD OF USING SAME

REFERENCE TO RELATED APPLICATIONS

This application claims the benefit of the filing date of PCT Patent Application Serial No. PCT/CN2015/000069 filed on Jan. 30, 2015, entitled "ACHILLES TENDON SUTURE APPARATUS AND METHOD OF USING SAME". The teachings of the entire referenced application are incorporated herein by reference.

FIELD OF THE INVENTION

The invention relates to the field of surgical medical appliance. More specifically, the invention relates to an Achilles tendon suture apparatus and a method of using the same.

BACKGROUND OF THE INVENTION

Rupture of Achilles tendon is a fracture of the Achilles tendon tissue caused by sport injury, cutting or chopping. The conventional surgical operation of the Achilles tendon suture is an opening surgical operation, and it needs to cut the skin to reveal the normal Achilles tendon portion and then suture the broken Achilles tendon by Bunnel, Kessler, 8 shaped suture and other common suture method. This opening surgical method is a reliable method for repairing Achillies tendon, but the incision of the surgical operation usually has a length up to 10 cm-15 cm, which can cause the harm to patients and cause the condition of disunion of the wounded area and infection. Furthermore, this method needs to peel off the tendon sheath, which can badly destroy the blood feeding of the Achilles tendon tissue and cause the complications of re-fracture of Achilles tendon, skin necrosis, infection, ankylosis and so on.

For relieving the distress of the patient, surgeons begin using the percutaneous micro-invasional suture surgery to suture Achillies tendon. This micro-invasional suture surgery only needs to make 6 small incisions on both sides of Achilles tendon, the broken Achilles tendon can be sutured percutaneously through the small incisions. The suturing effect of Achilles tendon of the micro-invasional surgery is the same as that of the conventional opening surgery, and the incision is short, the trauma is small, and the potentiality of the complications is reduced. But the percutaneous micro-invasional suture can't proceed under direct viewing, so the operation is very difficult, the repairing quality of the broken ends aren't reliable, even the sural nerve could be damaged to.

Bunnel suture method is a repairing method recognized by clinical which can offer enough strength for Achilles tendon repair. But it's operation is complicated, and the percutaneous suture is difficult, so it is difficult to obtain good result only by surgeon's hands operation. Now, the current clinical minimally invasive percutaneous suture surgical operation for Achilles tendon suture is usually carried out by the percutaneous suture device in combination with 8 shaped suturing method.

A suturing thread guiding apparatus for Achilles tendon suture is disclosed in the patent of CN201020522288.6 titled by " Suturing Thread Guiding Apparatus for Achilles Tendon Suture", in which an Achilles tendon suturing thread is directed through guiding holes of guiding arms which are located in one line, After many Achilles tendon suturing threads have been passed through the guiding holes, the suturing thread guiding apparatus is withdrawn. After the distal end and the proximal end of Achilles tendon have sutured together, the suturing thread is tighten, and the suturing threads of the distal end and the proximal end are tied a knot. Damage to nerve is avoided effectively by the percutaneous suturing apparatus in combination with 8 shaped suturing method, but Achilles tendon tissue is liable to be cut by the suturing threads, which cause the damage to Achilles tendon. Because there are many thread knots in the interrupt end, each suturing thread is strained variably and tightened asynchronously, therefore the Achilles tendon is liable to be torn, and the suturing strength is bad.

A guiding apparatus for repairing broken Achilles tendon is disclosed in the patent of CN201120262786.6 titled by "Medical Guiding Apparatus for Repairing Broken Achilles Tendon". In Achilles tendon suturing, the guiding apparatus is needed to be placed into Achilles tendon from the broken position, and the broken end of Achilles tendon must be placed between the inside of two positioning rods. A guider for passing a needle is used to pass 3 suturing threads in parallel, and two ends of the suturing threads are left outside the skin. The same procedure is taken place for the distal end of the broken Achilles tendon. Then the suturing threads are involuted and tied knots correspondingly. Box suture method as seen in FIG. 1(c) is adopted in this way, but the direct puncturing and suturing often cause damage to the sural nerve, which causes secondary injury to the patient.

Although the damage to the sural nerve due to Box suture method is avoided by utilizing Bunnel suture method, the final thread ends are placed at the middle of the broken Achilles tendon because the threads are diagonal pull threads, which can affect the healing of Achilles tendon.

Now, there is urgent need for an assistant apparatus for Achilles tendon suture which can overcome the defect of the prior art, avoid the danger of cutting Achilles tendon tissue, damaging to the sural nerve, high incidence of complications and the like which could occur possibly in the course of suturing, realize the rapid and safe suture of Achilles tendon, and relieve the pain of the patients.

SUMMARY OF THE INVENTION

In order to overcome the defect of the existing assistant apparatus for Achilles tendon suture, improve the safety and effectiveness of Achilles tendon suture, reduce the risk of incision infection, and decrease the damage to the sural nerve, according to the present invention, there is provided an Achilles tendon suture apparatus and a method for suturing broken Achilles tendon using the Achilles tendon suture apparatus.

According to an aspect of the present invention, there is provided an Achilles tendon suture apparatus which includes a first support and a second support, a distance regulating device, a first guiding sleeve, a second guiding sleeve, a first positioning barrel, a second positioning barrel and a tendon sheath cutter, and the first support and the second support are both with U type structure;

The first support and the second support are connected by the distance regulating device;

A first positioning hole is provided in the outer arm of the first support, a first guiding hole is provided in the inner arm of the first support;

A second positioning hole is provided in the outer arm of the second support, a second guiding hole is provided in the inner arm of the second support;

The centers of the first positioning hole, the first guiding hole, the second positioning hole and the second guiding hole are in a straight line;

The rear end of the first guiding sleeve is fixed in the outer arm of the first support by the first positioning hole, the front end of the first guiding sleeve matches with the first guiding hole;

The rear end of the second guiding sleeve is fixed in the outer arm of the second support by the second positioning hole, the front end of the second guiding sleeve matches with the second guiding hole;

The first positioning barrel is placed inside the first guiding sleeve and matches with the first guiding sleeve; or the tendon sheath cutter is placed inside the first guiding sleeve and matches with the first guiding sleeve, and the front end of the tendon sheath cutter is protruded out of the front end of the first guiding sleeve;

The second positioning barrel is placed inside the second guiding sleeve and matches with the second guiding sleeve; or the tendon sheath cutter is placed inside the second guiding sleeve and matches with the second guiding sleeve, and the front end of the tendon sheath cutter is protruded out of the front end of the second guiding sleeve;

There are provided through holes matching with an Achilles tendon suturing needle in both the first positioning barrel and the second positioning barrel;

The central axis of the through hole in the first positioning barrel and the central axis of the through hole in the second positioning barrel aren't in a straight line;

The front end of the tendon sheath cutter includes a spine portion, a cutting portion and a guiding portion;

The spine portion is used to pierce the tendon sheath;

The cutting portion is used to cut the tendon sheath;

The guiding portion connects to the rear end of the tendon sheath cutter for expanding the tendon sheath cut by the cutting portion.

According to a specific embodiment of the present invention, the central axis of the through hole in the first positioning barrel is coincident with the central axis of the first positioning barrel; the central axis of the through hole in the second positioning barrel is parallel to the central axis of the second positioning barrel.

According to another specific embodiment of the present invention, the cutting portion of the front end of the tendon sheath cutter has a cross section of diamond, a first internal angle of the diamond is 10°-60°, the two edges of the first internal angle are used to cut the tendon sheath.

According to yet another specific embodiment of the present invention, the spine portion is a taper, the apex angle of the taper is 60°-90°.

According to yet another specific embodiment of the present invention, the front end of the tendon sheath cutter has a length of 1.2 cm-1.8 cm.

According to yet another specific embodiment of the present invention, an included angle of the guiding portion is 30°-45°.

According to another aspect of the present invention, there is provided a method of using an Achilles tendon suture apparatus, the method includes following steps:

a) Touch the broken position of Achilles tendon through a skin surface, and make an incision at the broken position to reveal the proximal end and the distal end of broken Achilles tendon;

b) Clamp the proximal end of the Achilles tendon and pull it out to the position of the incision;

c) Insert the inner arm of the first support of the Achilles suture apparatus and the inner arm of the second support of the Achilles suture apparatus into the tendon sheath, and let the outer side of the inner arm of the first support and the outer side of the inner arm of the second support cling to the inner wall of the tendon sheath by regulating the distance regulating device;

d) Make a pincers-type incision in the skin surface along the first positioning hole of the outer arm of the first support, and push away the sural nerve at the pincers-type incision;

Make a pincers-type incision in the skin surface along the second positioning hole of the outer arm of the second support, and push away the sural nerve at the pincers-type incision;

e) Put the tendon sheath cutter into the first guiding sleeve, let the first guiding sleeve go through the first positioning hole, and obtusely pierce the tendon sheath by using the spine portion of the tendon sheath cutter;

Put the tendon sheath cutter into the second guiding sleeve, let the second guiding sleeve go through the second positioning hole, and obtusely pierce the tendon sheath by using the spine portion of the tendon sheath cutter, f) Push the Achilles tendon suture apparatus up and down along the running direction of Achilles tendon, cut the tendon sheath by the cutting portion of the tendon sheath cutter, and expand the cut tendon sheath by the guiding portion of the tendon sheath cutter;

g) Insert the first guiding sleeve further along the tendon sheath cutter, let the front end of the first guiding sleeve match with the first guiding hole in the inner arm of the first support, and remove the tendon sheath cutter;

Insert the second guiding sleeve further along the tendon sheath cutter, let the front end of the second guiding sleeve match with the second guiding hole in the inner arm of the second support, and remove the tendon sheath cutter;

h) Locate the first positioning barrel inside the first guiding sleeve cooperatively;

Locate the second positioning barrel inside the second guiding sleeve cooperatively;

i) Pass a suturing needle through the through holes of the first positioning barrel and the second positioning barrel in proper order, and grip the proximal end of Achilles tendon by means of the transverse Bunnel suture method;

j) Pull out the inner arm of the Achilles tendon suture apparatus from the incision, and lead out the suturing thread from the incision;

The Achilles tendon suture apparatus is an Achilles tendon suture apparatus according to anyone of claims 1-7.

According to a specific embodiment of the present invention, in the step a), the incision has a length of 1.2 cm-1.8 cm.

According to another specific embodiment of the present invention, in the step d), the pincers-type incision has a length of 4 mm-6 mm.

According to yet another specific embodiment of the present invention, in the step g), the tendon sheath is cut by the cutting portion of the tendon sheath cutter for a length of 0.8 cm-1.7 cm.

According to yet another aspect of the present invention, there is provided an Achilles tendon suture apparatus which includes a first support and a second support, a distance regulating device, a first guiding sleeve and a second guiding sleeve, and the first support and the second support are both with U type structure;

The first support and the second support are connected by the distance regulating device;

A first positioning hole is provided in the outer arm of the first support, a first guiding hole is provided in the inner arm of the first support;

A second positioning hole is provided in the outer arm of the second support, a second guiding hole is provided in the inner arm of the second support;

The centers of the first positioning hole, the first guiding hole, the second positioning hole and the second guiding hole are in a straight line;

The rear end of the first guiding sleeve is fixed in the outer arm of the first support by the first positioning hole, the front end of the first guiding sleeve matches with the first guiding hole;

The rear end of the second guiding sleeve is fixed in the outer arm of the second support by the second positioning hole, the front end of the second guiding sleeve matches with the second guiding hole;

There are provided through holes in both of the first guiding sleeve and the second guiding sleeve for matching with Kirschner wire;

The front end of the inner arm of the first support bends in the direction of the second support, and the top of the front end of the inner arm of the first support is flexible;

The front end of the inner arm of the second support bends in the direction of the first support, and the top of the front end of the inner arm of the second support is flexible.

Accord to a specific embodiment of the present invention, the bending degree of the front end of the inner arm of the first support is the same as the bending degree of the front end of the inner arm of the second support.

Accord to another specific embodiment, the top of the front end of the inner arm of the first support has a thickness of 0.3 mm-1.0 mm;

The top of the front end of the inner arm of the second support has a thickness of 0.3 mm-1.0 mm.

According to yet another aspect of the present invention, there is provided a method of using an Achilles tendon suture apparatus, the method includes following steps:

a) Touch the broken position of Achilles tendon through a skin surface, and make an incision at the broken position to reveal the proximal end and the distal end of broken Achilles tendon;

b) Push the Achilles tendon suture apparatus into the incision toward the distal end of Achilles tendon, and let the inner arm of the first support of the Achilles tendon suture apparatus and the inner arm of the second support of the Achilles tendon suture apparatus cling to the calcaneus;

c) Make a pincers-type incision in the skin surface along the first positioning hole of the outer arm of the first support, and push away the sural nerve at the pincers-type incision;

Make a pincers-type incision in the skin surface along the second positioning hole of the outer arm of the second support, and push away the sural nerve at the pincers-type incision;

d) Let the front end of the first guiding sleeve go through the first positioning hole and then match with the first guiding hole;

Let the front end of the second guiding sleeve go through the second positioning hole and then match with the second guiding hole;

e) Bore the calcaneus through the first guiding sleeve and the second guiding sleeve respectively, and establish a suturing passageway;

f) Pass a suturing thread through the suturing passageway;

g) Pull out the inner arm of the Achilles tendon suture apparatus from the incision, and lead out the suturing thread from the incision;

The Achilles tendon suture apparatus used in the steps b)-g) is an Achilles tendon suture apparatus according to anyone of claims 12-14.

According to a specific embodiment of the present invention, in the step a), the incision has a length of 1.2 cm-1.8 cm.

According to another specific embodiment of the present invention, in the step d), the pincers-type incision has a length of 4 mm-6 mm.

According to the present invention, there is provided an Achilles tendon suture apparatus which includes a first support, a second support, a distance regulating device, a first guiding sleeve, a second guiding sleeve, a first positioning barrel and a second positioning barrel, and both the first support and the second support have U type arms. When used, inner arms of the U type arms of two supports can be inserted between the tendon sheath and Achilles tendon, and the outer side of the inner arms can cling to the inner wall of the tendon sheath by the distance regulating device.

After the flexible tendon sheath is expanded, a pincers-type incision is made in the skin surface through positioning holes of outer arms of two supports. Because sural nerve is flexible in it's running direction, the sural nerve can be pushed away easily by hemostatic forceps and the like, therefore during the following suture, the adverse effect on the nerve is avoided.

The tendon sheath cutter is used with the guiding sleeve cooperatively. Because the guiding sleeve has circular structure, when it covers the outside of the tendon sheath cutter, it is avoided that other tissue of the patient is destroyed by the tendon sheath cutter. The front end of the tendon sheath cutter has a specific design, and it includes a spine portion, a cutting portion and a guiding portion. The spine portion can pierce the tendon sheath easily, the cutting portion can cut the tendon sheath, and the guiding portion can expand the cut tendon sheath to let the wounds of cutting up and down be circular, so that the guiding sleeve can further match with the positioning hole. By means of specific dimensional design, favorable operating effect is achieved by the three portions of the front end of the tendon sheath cutter, and at the same time, other tissue can't be damaged to.

After positioning the guiding sleeve cooperatively, a suturing passageway is established, in which the positioning barrel is inserted. By means of passing a needle and threads through the through hole in the middle of the positioning hole, the tendon sheath is sutured. Preferentially, the centers of the through holes of two positioning barrels aren't in a straight line, and the suturing threads can't be coincident by means of the transverse Bunnel suture method, so the suturing effect is reliable. This Achilles tendon suture apparatus is suitable for suturing the proximal end of Achilles tendon. For the distal end of Achilles tendon, if the distance between the distanl end of broken Achilles tendon and the stop point of the calcaneus is more than 2 cm, this Achilles tendon suture apparatus may be used for suturing Achilles tendon.

According to the present invention, there is provided another Achilles tendon suture apparatus which has a first support, a second support, a distance regulating device, a first guiding sleeve and a second guiding sleeve, and both the first support and the second support have U type arms. When used, the Achilles tendon suture apparatus is pushed toward the distal end of Achilles tendon at the incision, and the distance regulating device is regulated, so that the inner arm of the first support of the Achilles tendon suture apparatus and the inner arm of the second support of the Achilles tendon suture apparatus cling to the calcaneus.

The front end of the inner arm of the first support bends in the direction of the second support, and the top of the front end of the inner arm of the first support is flexible; the front end of the inner arm of the second support bends in the direction of the first support, and the top of the front end of the inner arm of the second support is flexible. The structure of the front ends of two supports is similar to that of a periosteum elevator, the purpose of the flexible structure of the top of the front end of the inner arm is to elevate the periosteum from the bone surface. The relatively bent structure of two front ends can cling to the bone surface more tightly in the course of the supports advancing, and the periosteum can't be pierced to cause secondary injury. This Achilles tendon suture apparatus is mainly suitable for suturing the distal end of Achilles tendon. If the distance between a broken point of the distal end of Achilles tendon and the stop point of the calcaneus is no more than 2 cm, favorable suturing effect is achieved by adopting this Achilles tendon suture apparatus.

Achilles tendon's fracture is usually taken place at the position where a broken point of the distal end of Achilles tendon is near the stop point of the calcaneus, so two Achilles tendon suture apparatuses proposed by the present invention are usually combined to use, therefore favorable suturing effect is achieved. By using the method of the transverse Bunnel suture is avoided that Achilles tendon is cut by the suturing thread when suturing, and the sural nerve of the patient is protected.

BRIEF DESCRIPTION OF THE FIGURES

Other features, objects and advantages of the present invention will become more apparent by reading the detailed description of non-restrictive embodiments taken in conjunction with the accompanying figures.

In the figures, same or like reference characters are used to represent same or like parts.

Figure 1:
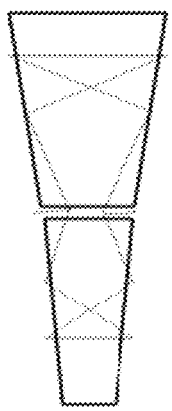
FIG. 1(a) is a schematic view showing the Bunnel suture method.
FIG. 1(b) is a schematic view showing the transverse Bunnel suture method adopted by the present invention.
FIG. 1(c) is a schematic view showing the Box suture method.
Figure 1:
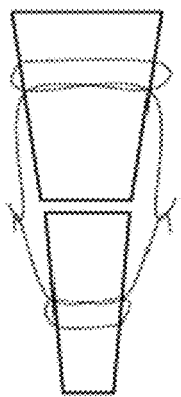
Figure 1:
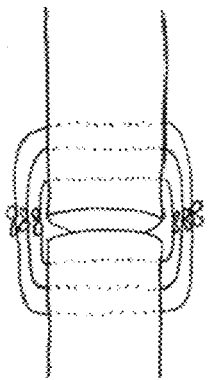

The reference characters are listed in the following table:

| 10 | first support | 20 | second support |
|---|---|---|---|
| 3 | distance regulating device | 4 | tendon sheath cutter |
| 5 | suturing needle | 6 | Kirschner wire |
| 11 | first positioning hole | 21 | second positioning hole |
| 12 | first guiding hole | 22 | second guiding hole |
| 13 | first guiding sleeve | 23 | second guiding sleeve |
| 14 | first position barrel | 24 | second positioning barrel |
| 15 | front end of inner arm of first support | 25 | ront end of inner arm of second support |
| 41 | front end of tendon sheath cutter | 42 | rear end of tendon sheath cutter |
| 411 | spine portion | 412 | cutting portion |
| 413 | guiding portion | | |

DETAILED DESCRIPTION

Hereinafter, many different embodiments or examples will be described for embodying different structure of the present invention. For the purpose of simplifying the disclosure of the present invention, components and installation of specific examples are described hereinafter. Furthermore, reference numbers and/or letters may be repeated in the different embodiments of the present invention. The purpose of this repetition is simplification and clarity, and there is no purpose of indicating the relation of the embodiments and/or installation. It is noted that the components shown in the figures can be drawn not to scale. The well-known parts and processing technique and technology are omitted in order not to unnecessarily limit the present invention.

Figure 2:
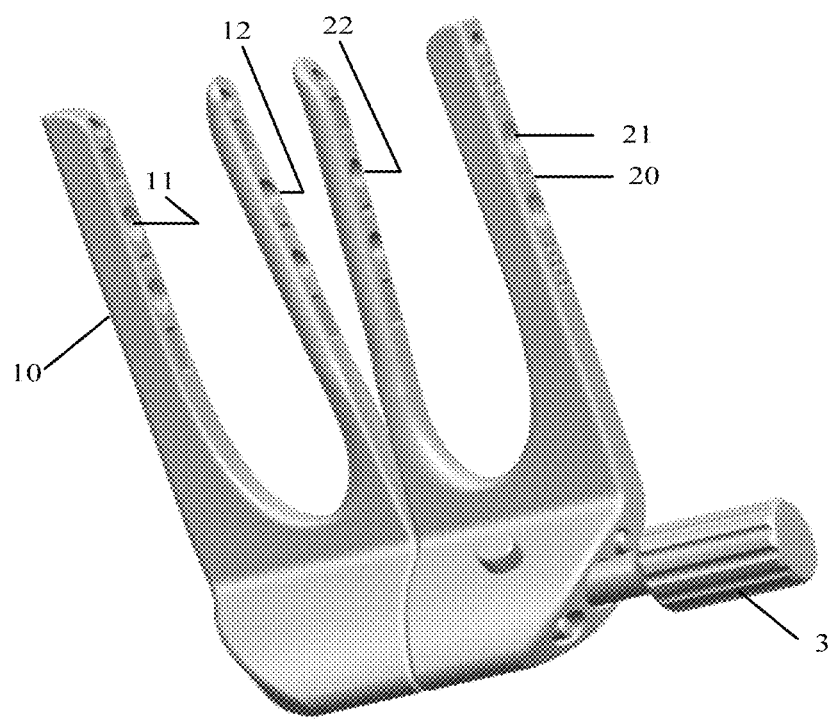
FIG. 2 is a schematic view showing the combination of the first support and the second support in an Achilles tendon suture apparatus provided by the present invention.
Figure 3:
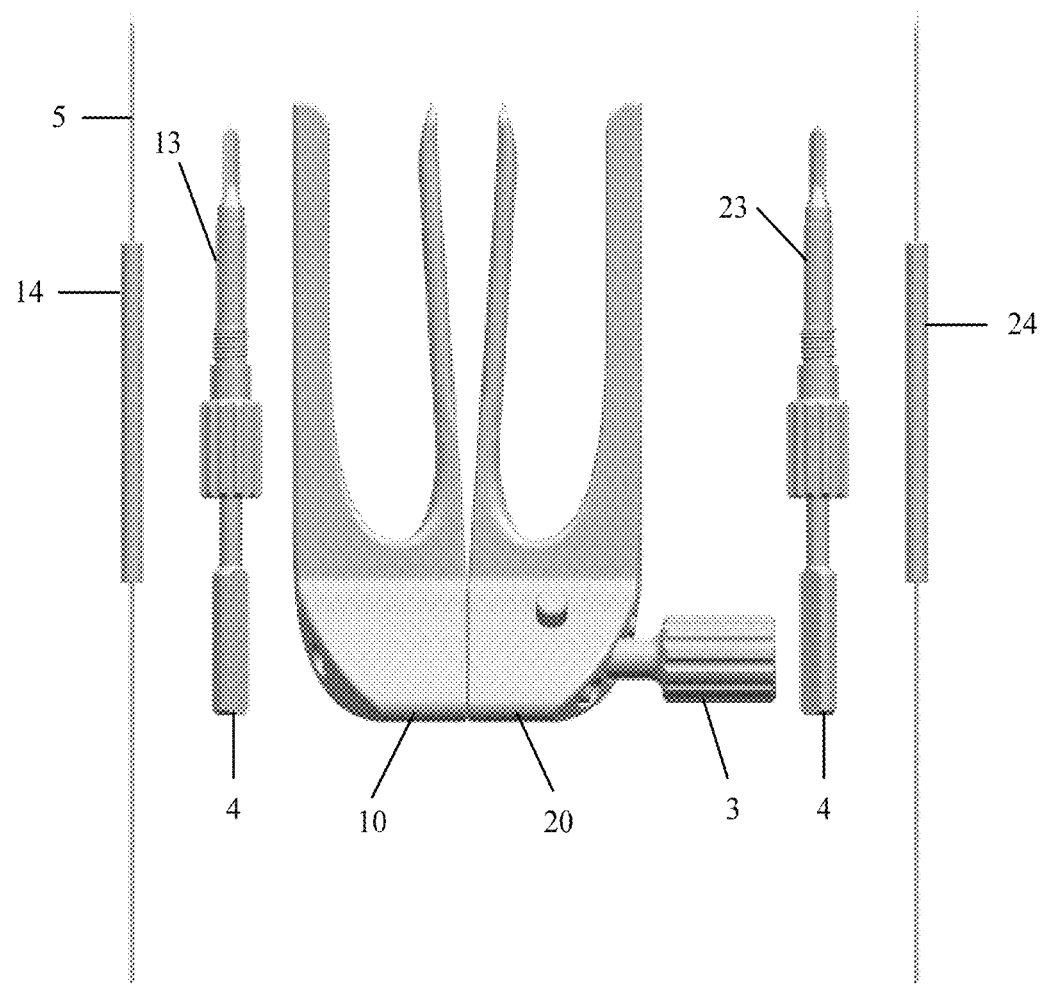
FIG. 3 is a structural schematic view showing a specific embodiment of the Achilles tendon suture apparatus provided by the present invention.

With reference to FIG. 2 and FIG. 3, An Achilles tendon suture apparatus provided by the present invention includes a first support 10 with U type structure, a second support 20 with U type structure, a distance regulating device 3, a first guiding sleeve 13, a second guiding sleeve 23, a first positioning barrel 14, a second positioning barrel 24 and a tendon sheath cutter 4.

The first support 10 and the second support 20 are connected by the distance regulating device 3. The connection can be a bayonet connection or a screw connection. Preferentially, the screw connection is adopted in the present invention. The position of the first support 10 and the second support 20 is regulated by rotating the distance regulating device 3. Preferentially, a positioning device can be added, so that the position of the first support 10 and the second support 20 is fixed by the positioning device when it is regulated to a suitable position.

A first positioning hole 11 is provided in the outer arm of the first support 10, a first guiding hole 12 is provided in the inner arm of the first support 10. A second positioning hole 21 is provided in the outer arm of the second support 20, a second guiding hole 22 is provided in the inner arm of the second support 20. The centers of the first positioning hole 11, the first guiding hole 12, the second positioning hole 21 and the second guiding hole 22 are in a straight line.

It is noted that there may be many sets of the first positioning holes 11, the first guiding holes 12, the second positioning holes 21 and the second guiding holes 22 for meeting the persons having different body height. When used, an optimum set can be chosen as required.

The rear end of the first guiding sleeve 13 is fixed in the outer arm of the first support by the first positioning hole 11, the front end of the first guiding sleeve 13 matches with the first guiding hole 12. A passageway is provided between the first positioning hole 11 and the first guiding hole 12 by the first guiding sleeve 13.

The rear end of the second guiding sleeve 23 is fixed in the outer arm of the second support by the second positioning hole 21, the front end of the second guiding sleeve 23 matches with the second guiding hole 22, A passageway is provided between the second positioning hole 21 and the second guiding hole 22 by the second guiding sleeve 23.

The first positioning barrel 14 is placed inside the first guiding sleeve 13 and matches with the first guiding sleeve 13; or the tendon sheath cutter 4 is placed inside the first guiding sleeve 13 and matches with the first guiding sleeve 13, and the front end of the tendon sheath cutter 4 is protruded out of the front end of the first guiding sleeve 13. Both the first positioning barrel 14 and the tendon sheath cutter 4 can match with the first guiding sleeve 13, so they can be chosen to use as required.

The second positioning barrel 24 is placed inside the second guiding sleeve 23 and matches with the second guiding sleeve 23; or the tendon sheath cutter 4 is placed inside the second guiding sleeve 23 and matches with the second guiding sleeve 23, and the front end of the tendon sheath cutter 4 is protruded out of the front end of the second guiding sleeve 23. Both the second positioning barrel 24 and the tendon sheath cutter 4 can match with the second guiding sleeve 23, so they can be chosen to use as required.

Figure 4:
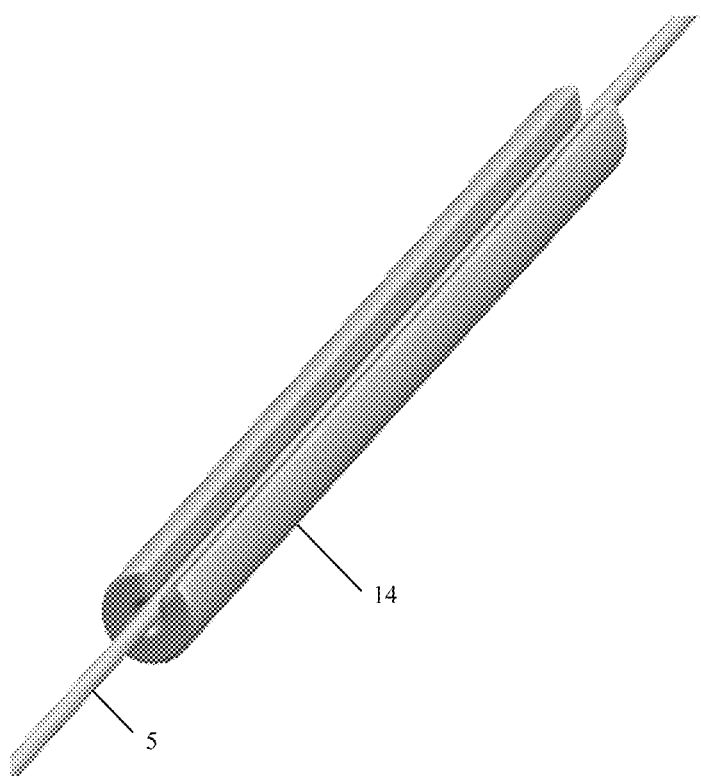
FIG. 4 is a structural schematic view showing a specific embodiment of the first positioning barrel.
Figure 5:
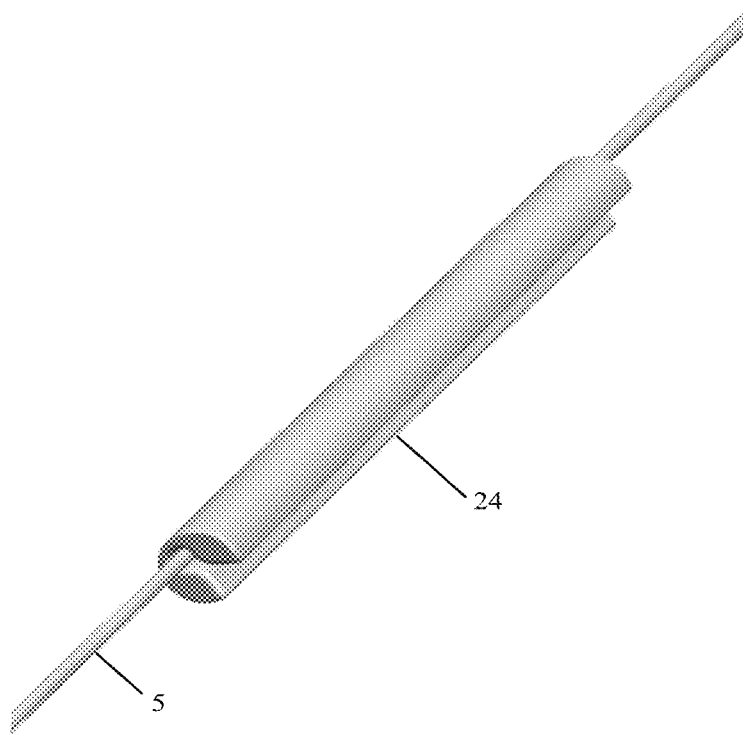
FIG. 5 is a structural schematic view showing a specific embodiment of the second positioning barrel.

There are provided through holes matching with an Achilles tendon suturing needle 5 in both the first positioning barrel 14 and the second positioning barrel 24. In order that the suturing threads can't be coincident during suturing, the central axis of the through hole in the first positioning barrel 14 and the central axis of the through hole in the second positioning barrel 24 aren't in a straight line. Preferentially, the central axis of the through hole in the first positioning barrel 14 is coincident with the central axis of the first positioning barrel 14, as see in FIG. 4. The central axis of the through hole in the second positioning barrel 24 is parallel to the central axis of the second positioning barrel 24, as see in FIG. 5.

Figure 6:
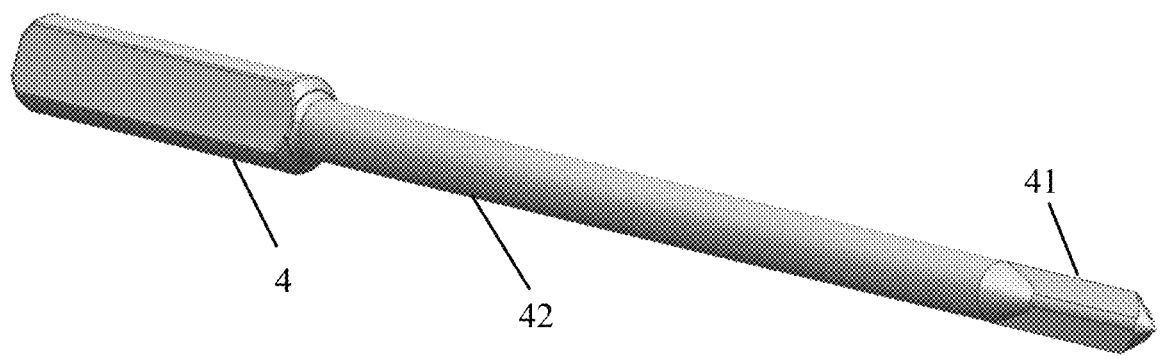
FIG. 6 is a structural schematic view showing a specific embodiment of the tendon sheath cutter.

As seen in FIG. 6, the tendon sheath cutter 4 is divided into the front end 41 of the tendon sheath cutter and the rear end 42 of the tendon sheath cutter. Preferentially, the front end 41 of the tendon sheath cutter has a length of 1.2 cm-1.8 cm, such as 1.2 cm, 1.5 cm or 1.8 cm. If the front end 41 of the tendon sheath cutter has an excess length and the guiding portion 413 can't expand the cut tendon sheath, the first guiding sleeve 13 and/or the second guiding sleeve 23 can't go through the cut tendon sheath and match with the first guiding hole 12 and/or the second guiding hole 22, therefore a guiding passageway can't be established in the case that the sural nerve could not be damaged to. If the front end 41 of the tendon sheath cutter is too short, it can't cut the tendon sheath effectively.

Figure 7:
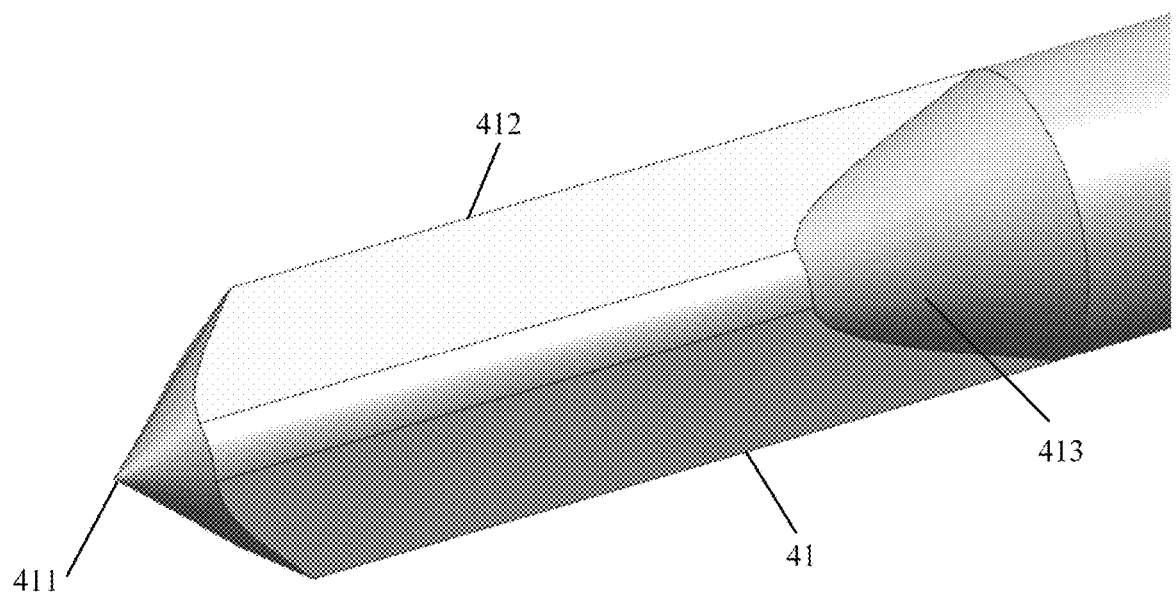
FIG. 7 is a structural schematic view showing a specific embodiment of the front end of the tendon sheath cutter.
Figure 8:
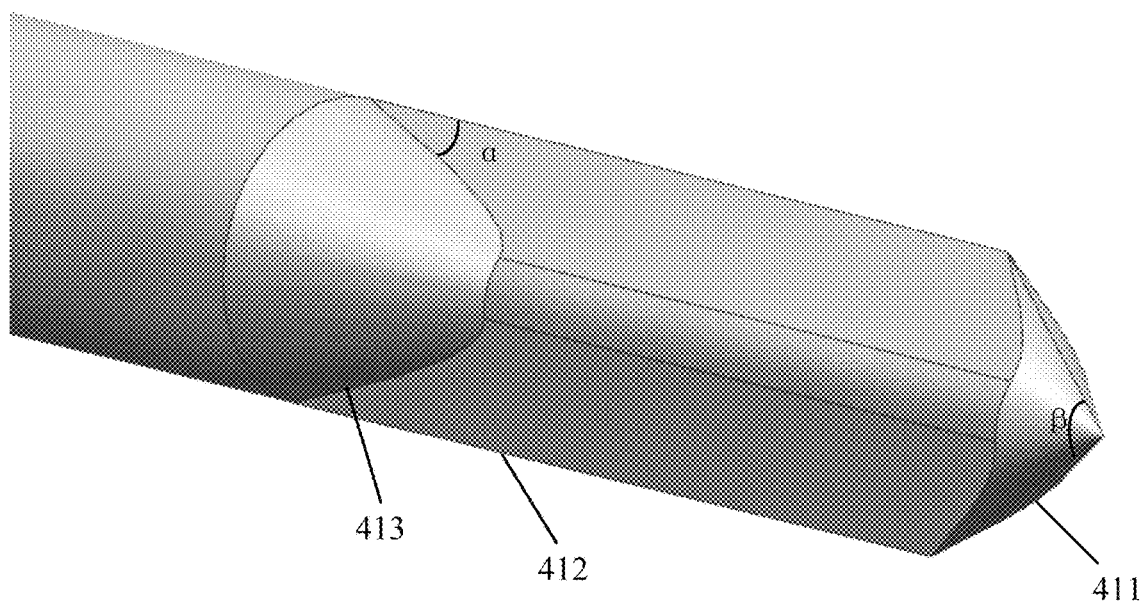
FIG. 8 is a structural schematic view showing another specific embodiment of the front end of the tendon sheath cutter.

With reference to FIG. 7 and FIG. 8, the front end 41 of the tendon sheath cutter includes a spine portion 411, a cutting portion 412 and a guiding portion 413.

The spine portion 411 is used to pierce the tendon sheath, the cutting portion 412 is used to cut the tendon sheath, the guiding portion 412 connects to the rear end 42 of the tendon sheath cutter for expanding the tendon sheath cut by the cutting portion 412.

Preferentially, the spine portion 411 is a taper, the apex angle β of the taper is 60°-90°, such as 60°, 75° or 90°. More preferentially, the apex angle β of the taper is 80°. If the apex angle β of the taper is too large, it is adverse to pierce the tendon sheath. If the apex angle of the taper is too small, it is too sharp, and there is a hidden trouble of safety.

Figure 9:
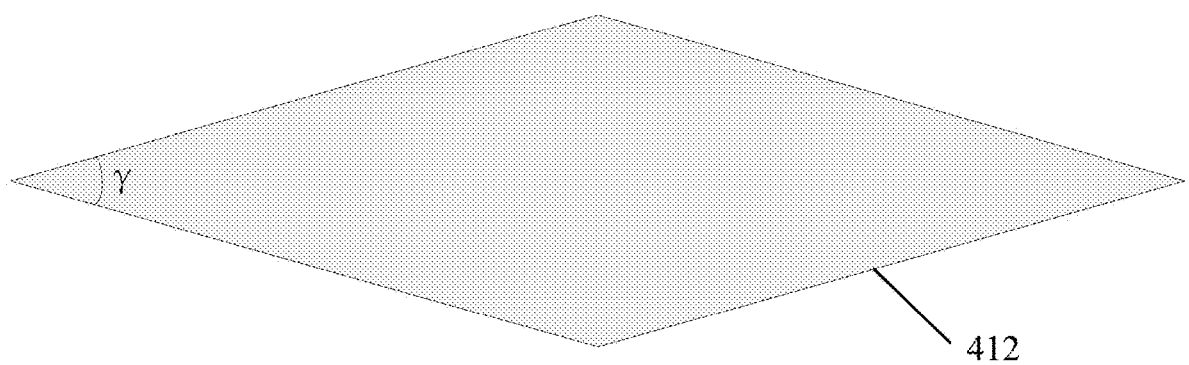
FIG. 9 is a structural schematic view showing a cross section of the cutting portion of the front end of the tendon sheath cutter.

With reference to FIG. 9, the cutting portion of the front end of the tendon sheath cutter has a cross section of diamond, a first internal angle γ of the diamond is 10°-60°. Preferentially, the first internal angle γ is 10°, 30° or 60°. More preferentially, the first internal angle γ is 53°. The two edges of the first internal angle γ are used to cut the tendon sheath. If the first internal angle γ is too small, the edges for cutting the tendon sheath is too sharp, and there is a hidden trouble of safety, it is liable to cause damage to the healthy tissue. If the first internal angle γ is too large, the edges for cutting the tendon sheath is too blunt to cut.

As seen in FIG. 8, an included angle α of the guiding portion is 30°-45°, preferentially, 30°, 40° or 45°. After Achilles tendon is cut by the cutting portion 412, the tendon sheath cutter 4 continues to be pushed forward, so that the guiding portion 413 enters into the cutting position, and the incision is expanded into a circle. The first guiding sleeve 13 and/or the second guiding sleeve 23 are pushed forward along the tendon sheath cutter 4 to match with the first guiding hole 12 and/or the second guiding hole 22. In this time, the guiding passageway is established outside the first guiding sleeve 13 and/or the second guiding sleeve 23 in the cut tendon sheath. Because the following operation such as suturing proceeds is taken place inside the guiding passageway, the tendon sheath and the surrounding sural nerve can't be damaged to.

The Achilles tendon suture apparatus the above is mainly suitable for suturing the proximal end of Achilles tendon, and if the distance between the distal end of broken Achilles tendon and the stop point of the calcaneus is more than 2 cm, this Achilles tendon suture apparatus is also suitable for suturing the distal end of Achilles tendon.

According to the present invention, there is provided another Achilles tendon suture apparatus which is mainly suitable for suturing the distal end of Achilles tendon when the distance between the distal end of broken Achilles tendon and the stop point of the calcaneus is no more than 2 cm. The Achilles tendon suture apparatus mainly suitable for suturing the distal end of Achilles tendon will be described in detail hereinafter.

Figure 10:
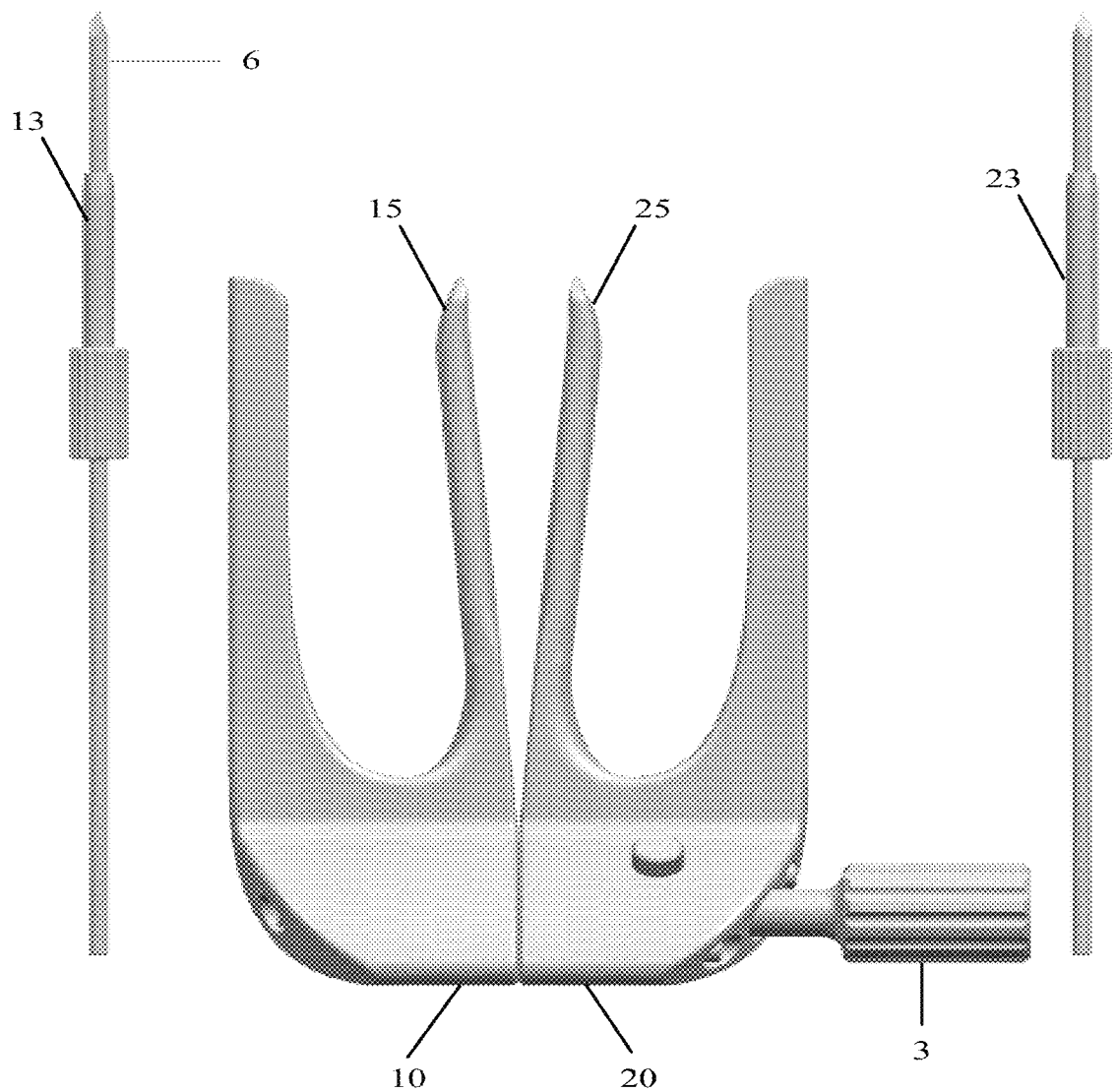
FIG. 10 is a structural schematic view showing another specific embodiment of the Achilles tendon suture apparatus provided by the present invention.

With reference to FIG. 10, the Achilles tendon suture apparatus includes a first support 10 with U type structure, a second support 20 with U type structure, a distance regulating device 3, a first guiding sleeve 13 and a second guiding sleeve 23.

The first support 10 and the second support 20 are connected by the distance regulating device 3. The connection can be a bayonet connection or a screw connection. Preferentially, the screw connection is adopted in the present invention. The position of the first support 10 and the second support 20 is regulated by rotating the distance regulating device 3. Preferentially, a positioning device can be added, so that the position of the first support 10 and the second support 20 is fixed by the positioning device when it is regulated to a suitable position.

A first positioning hole 11 is provided in the outer arm of the first support 10, a first guiding hole 12 is provided in the inner arm of the first support 10. A second positioning hole 21 is provided in the outer arm of the second support 20, a second guiding hole 22 is provided in the inner arm of the second support 20. The centers of the first positioning hole 11, the first guiding hole 12, the second positioning hole 21 and the second guiding hole 22 are in a straight line.

It is noted that there may be many sets of the first positioning holes 11, the first guiding holes 12, the second positioning holes 21 and the second guiding holes 22 for meeting the persons having different body height. When used, an optimum set can be chosen as required.

The rear end of the first guiding sleeve 13 is fixed in the outer arm of the first support 10 by the first positioning hole 11, the front end of the first guiding sleeve 13 matches with the first guiding hole 12. A passageway is provided between the first positioning hole 11 and the first guiding hole 12 by the first guiding sleeve 13.

The rear end of the second guiding sleeve 23 is fixed in the outer arm of the second support 20 by the second positioning hole 21, the front end of the second guiding sleeve 23 matches with the second guiding hole 22. A passageway is provided between the second positioning hole 21 and the second guiding hole 22 by the second guiding sleeve 23.

There are provided through holes in both the first guiding sleeve 13 and the second guiding sleeve 23 for matching with Kirschner wire. The Kirschner wire is adapted to pass suture threads into the calcaneus for suturing. It is known that today the Kirschner wire is adapted to fulfil this function usually, but if another suturing needle can fulfil this function, it can replace the Kirschner wire. And the present invention is not limited to the details.

The front end 15 of the inner arm of the first support 10 bends in the direction of the second support 20, and the top of the front end 15 of the inner arm of the first support 10 is flexible. The front end 25 of the inner arm of the second support bends in the direction of the first support 10, and the top of the front end 25 of the inner arm of the second support is flexible. Preferentially, the bending degree of the front end 15 of the inner arm of the first support is the same as the bending degree of the front end 25 of the inner arm of the second support.

When the Achilles tendon suture apparatus is inserted into the incision and pushed toward the distal end of Achilles tendon, and the inner arms of the first support 10 and the second support 20 cling to the calcaneus, the inner arms of two supports may cling to the calcaneus because the front ends of the inner arms of two supports bend relatively. When further advancing, the tops of the front ends of the inner arms are to elevate the periosteum from the calcaneus (the function is similar to that of a periosteum elevator), and the periosteum may cling to the outer sides of the inner arms of two supports. In prior art, the front ends of the inner arms of the first support 10 and the second support 20 bend in reverse direction respectively, when advancing, the expanding front ends of the inner arms of the supports may pierce the periosteum and cause secondary injury to the patient.

Preferentially, the top of the front end 15 of the inner arm of the first support has a thickness of 0.3 mm-1.0 mm, such as 0.3 mm, 0.6 mm or 1.0 mm. The top of the front end 25 of the inner arm of the second support has a thickness of 0.3 mm-1.0 mm, such as 0.3 mm, 0.6 mm or 1.0 mm.

Two Achilles tendon suture apparatuses provided by the present invention can be made of metal which can be used repeatedly and has a lower cost. For the purpose of safety and hygiene, the metal may be replaced of disposable and medical plastic material. More preferentially, the apparatuses have many sizes as required, so that they can meet the demands of different persons, such as adults, children and so on.

While two Achilles tendon suture apparatuses provided by the present invention have be described hereinbefore, methods of using the Achilles tendon suture apparatuses will be described hereinafter. First of all, a method of using the Achilles tendon suture apparatus which is mainly adapted to suturing the proximal end of Achilles tendon is described, the method includes following steps:

a) Touch the broken position of Achilles tendon through a skin surface, and make a transverse incision in the direction perpendicular to Achilles tendon or make a longitudinal incision in the direction parallel to Achilles tendon at the broken position to reveal the proximal end of broken Achilles tendon and the distal end of broken Achilles tendon. Preferentially, the incision has a length of 1.2 cm-1.8 cm, such as 1.2 cm, 1.5 cm or 1.8 cm. The length is enough if the incision allows for inserting the inner arms of Achilles tendon, so a large incision is unnecessary, which can diminish the wound of the patient effectively, promote the postoperative restoration of the patient and reduce the complications.

b) Clamp the proximal end of the Achilles tendon and pull it out to the position of the incision. Because Achilles tendon has resilience, once broken, it may shrink. For the purpose of better restoration after suturing, Achilles tendon needs be pulled out before suturing and put into a expanding state.

c) Insert the inner arm of the first support 10 of the Achilles suture apparatus and the inner arm of the second support 20 of the Achilles suture apparatus into a tendon sheath, and let the outer side of the inner arm of the first support 10 and the outer side of the inner arm of the second support 20 cling to the inner wall of the tendon sheath by regulating a distance regulating device 3. The tendon sheath is supported and put into a tight state for facilitating the following cutting.

d) Make a pincers-type incision in the skin surface along the first positioning hole 11 of the outer arm of the first support 10, and push away the sural nerve at the pincers-type incision. Make a pincers-type incision in the skin surface along the second positioning hole 21 of the outer arm of the second support 20, and push away the sural nerve at the pincers-type incision. In order to diminish the wound of the patient, the dimension of the incision is reduced as far as possible. But if the incision is too small, it is difficult for the following operation. So preferentially, the pincers-type incision has a length of 4 mm-6 mm, such as 4 mm, 5 mm or 6 mm.

Preferentially, hemostatic forceps are used to push away the sural nerve. Because the sural nerve is flexible, after touching the sural nerve, the hemostatic forceps can push away the sural nerve and can't pierce it.

e) Put the tendon sheath cutter 4 into the first guiding sleeve 13, let the first guiding sleeve 13 go through the first positioning hole 11, and obtusely pierce the tendon sheath by using the spine portion of the tendon sheath cutter. Put the tendon sheath cutter 4 into the second guiding sleeve 23, let the second guiding sleeve 23 go through the second positioning hole 21, and obtusely pierce the tendon sheath by the spine portion 411 of the tendon sheath cutter 4. Preferentially, two actions need to be performed at the same time.

f) Push the Achilles tendon suture apparatus up and down along the running direction of Achilles tendon, cut the tendon sheath by the cutting portion 412 of the tendon sheath cutter. The incision is an upright incision. Preferentially, the Achilles tendon is cut by a length of 0.8 cm-1.7 cm by the cutting portion 412 of the tendon sheath cutter, such as 0.8 cm, 1.3 cm or 1.7 cm.

And then push the Achilles tendon suture apparatus further, so that it's guiding portion 4 enters into the upright incision. Expand the cut tendon sheath by the guiding portion 413 of the tendon sheath cutter 4 and then expand the incision into a circle.

g) Insert the first guiding sleeve 13 further along the tendon sheath cutter 4, let the front end of the first guiding sleeve 13 match with the first guiding hole 12 in the inner arm of the first support 10. Because the incision has expanded into a circle by the guiding portion 413 of the tendon sheath cutter 4, the first guiding sleeve 13 can advance along the tendon sheath cutter 4 easily and enter into the circular incision, and the tendon sheath is placed outside the circular incision. After the front end of the first guiding sleeve 13 matches with the first guiding hole 12, a guiding passageway is established. At this time, the tendon sheath cutter 4 can be removed.

Insert the second guiding sleeve 23 further along the tendon sheath cutter 4, let the front end of the second guiding sleeve 23 match with the second guiding hole 22 in the inner arm of the second support 20. Because the incision has expanded into a circle by the guiding portion 413 of the tendon sheath cutter 4, the second guiding sleeve 23 can advance along the tendon sheath cutter 4 easily and enter into the circular incision, and the tendon sheath is placed outside the circular incision. After the front end of the second guiding sleeve 23 matches with the second guiding hole 22, a guiding passageway is established. At this time, the tendon sheath cutter 4 can be removed.

h) Locate the first positioning barrel 14 inside the first guiding sleeve 13 cooperatively. Locate the second positioning barrel 24 inside the second guiding sleeve 23 cooperatively. The central axis of the through hole in the first positioning barrel 14 and the central axis of the through hole in the second positioning barrel 24 aren't in a straight line, so it is avoided that the suturing threads are coincident when adopting the transverse Bunnel suture method.

Preferentially, the central axis of the through hole in the first positioning barrel is coincident with the central axis of the first positioning barrel, and the central axis of the through hole in the second positioning barrel is parallel to the central axis of the second positioning barrel.

i) Pass a suturing needle through the through holes of the first positioning barrel 14 and the second positioning barrel 24 in proper order, and grip the proximal end of Achilles tendon by means of the transverse Bunnel suture method. The transverse Bunnel suture method adopted by the present invention is shown in FIG. 1(*b*).

j) Pull out the inner arm of the Achilles tendon suture apparatus from the incision, and lead out the suturing thread from the incision.

In the following, a method of using the Achilles tendon suture apparatus which is mainly adapted to suturing the distal end of Achilles tendon is described, the method includes following steps:

a) Touch the broken position of Achilles tendon through a skin surface, and make a transverse incision in the direction perpendicular to Achilles tendon or make a longitudinal incision in the direction parallel to Achilles tendon at the broken position to reveal the proximal end of broken Achilles tendon and the distal end of broken Achilles tendon. Preferentially, the incision has a length of 1.2 cm-1.8 cm, such as 1.2 cm, 1.5 cm or 1.8 cm. The length is enough if the incision allows for inserting the inner arms of Achilles tendon, so a large incision is unnecessary, which can diminish the wound of the patient effectively, promote the postoperative recovery of the patient and reduce the complications.

b) Push the Achilles tendon suture apparatus into the incision toward the distal end of Achilles tendon, and let the inner arm of the first support 10 of the Achilles tendon suture apparatus and the inner arm of the second support 20 of the Achilles tendon suture apparatus cling to the calcaneus.

When the Achilles tendon suture apparatus is inserted into the incision and pushed toward the distal end of Achilles tendon, and the inner arms of the first support 10 and the second support 20 cling to the calcaneus, the inner arms of two supports may cling to the calcaneus because the front ends of the inner arms of two supports bend relatively. When further advancing, the tops of the front ends of the inner arms are to elevate the periosteum from the calcaneus (the function is similar to that of a periosteum elevator), and the periosteum may cling to the outer sides of the inner arms of two supports.

In prior art, the front ends of the inner arms of the first support 10 and the second support 20 bend in reverse direction respectively, when the Achilles tendon suture apparatus advance, the expanding front ends of the inner arms of the supports may pierce the periosteum and cause secondary injury to the patient. The destruction of the periosteum can be avoided by the Achilles tendon suture apparatus of the present invention.

c) Make a pincers-type incision in the skin surface along the first positioning hole 11 of the outer arm of the first support 10, and push away the sural nerve at the pincers-type incision. Make a pincers-type incision in the skin surface along the second positioning hole 21 of the outer arm of the second support 20, and push away the sural nerve at the pincers-type incision. In order to diminish the wound of the patient, the dimension of the incision is reduced as far as possible. But if the incision is too small, it is difficult for the following operation. So preferentially, the pincers-type incision has a length of 4 mm-6 mm, such as 4 mm, 5 mm or 6 mm.

Preferentially, hemostatic forceps are used to push away the sural nerve. Because the sural nerve is flexible, after touching the sural nerve, the hemostatic forceps can push away the sural nerve and can't pierce it.

d) Let the front end of the first guiding sleeve 13 go through the first positioning hole 11 and then match with the first guiding hole 12. Let the front end of the second guiding sleeve 23 go through the second positioning hole 21 and then match with the second guiding hole 22.

e) Bore the calcaneus through the first guiding sleeve 13 and the second guiding sleeve 23 respectively, and establish a suturing passageway.

f) Pass a Kirschner wire 6 with a suturing thread through the suturing passageway.

g) Pull out the inner arm of the Achilles tendon suture apparatus from the incision, and lead out the suturing thread from the incision.

In the course of a specific surgical operation, what we just need is to draw out the proximal suturing thread and the distal suturing thread from the incision, pull tightly and then tie a knot, and intensively suture the proximal end of the Achilles tendon and the distal end of the Achilles tendon, then suture the surrounding tissue of the Achilles tendon, finally close the incision and pressurize and bind up it.

The Achilles tendon suture apparatus provided by the present invention has a simple structure, lower cost and wide applicability, and it is easy to operate. When a broken Achilles tendon is sutured by the Achilles tendon suture apparatus of the present invention, we can avoid the danger of cutting Achilles tendon tissue by the suturing thread and damaging the sural nerve, so the Achilles tendon is sutured rapidly and safely, and the patients can relieve the pain and recovery rapidly after operation.

Although the exemplary embodiments and their advantages have been described in detail, it should be understood that various changes, substitutions, and alterations can be made in these embodiments without departing from the spirit of the invention and the protected scope of the appended claims. With regard to the other examples, as one of ordinary skill in the art will readily appreciate, the sequence of the processing steps can be varied without departing from the protected scope of the invention.

Moreover, the scope of the present application is not intended to be limited to the particular embodiments of the process, machine, manufacture, composition of matter, means, methods, and steps described in the specification. As one of ordinary skill in the art will readily appreciate from the disclosure of the present disclosure, the processes, machines, manufacture, compositions of matter, means, methods, or steps presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. An Achilles tendon suture apparatus comprising a first support and a second support, a distance regulating device, a first guiding sleeve, a second guiding sleeve, a first positioning barrel, a second positioning barrel and a tendon sheath cutter, wherein:
   the first support and the second support both have a U type structure;
   the first support and the second support are connected by the distance regulating device;
   a first positioning hole is provided in an outer arm of the first support, a first guiding hole is provided in an inner arm of the first support;
   a second positioning hole is provided in an outer arm of the second support, a second guiding hole is provided in an inner arm of the second support;
   the centers of the first positioning hole, the first guiding hole, the second positioning hole and the second guiding hole are in a straight line;
   the first guiding sleeve has a rear end fixed in the outer arm of the first support by the first positioning hole, and a front end fitted into the first guiding hole, the second guiding sleeve has a rear end fixed in the outer arm of the second support by the second positioning hole, and a front end of fitted into the second guiding hole;
   the first positioning barrel is placed inside the first guiding sleeve and slidably coupled with the first guiding sleeve, or the tendon sheath cutter is placed inside the first guiding sleeve and slidably coupled with the first guiding sleeve, and a front end of the tendon sheath cutter is protruded out of the front end of the first guiding sleeve;
   the second positioning barrel is placed inside the second guiding sleeve and matches with the second guiding sleeve, or the tendon sheath cutter is placed inside the second guiding sleeve and matches with the second guiding sleeve, and the front end of the tendon sheath cutter is protruded out of the front end of the second guiding sleeve;
   there are provided through holes matching with an Achilles tendon suturing needle in both the first positioning barrel and the second positioning barrel;
   wherein the central axis of the through hole in the first positioning barrel and the central axis of the through hole in the second positioning barrel aren't in a straight line; wherein the front end of the tendon sheath cutter includes a spine portion, a cutting portion and a guiding portion; wherein the spine portion is used to pierce the tendon sheath; wherein the cutting portion is used to cut the tendon sheath; wherein the guiding portion connects to a rear end of the tendon sheath cutter for expanding the tendon sheath cut by the cutting portion.

2. The Achilles tendon suture apparatus according to claim 1, wherein:
   the central axis of the through hole in the first positioning barrel is coincident with the central axis of the first positioning barrel;
   the central axis of the through hole in the second positioning barrel is parallel to the central axis of the second positioning barrel.

3. The Achilles tendon suture apparatus according to claim 1, wherein: the cutting portion of the front end of the tendon sheath cutter has a cross-sectional shape of diamond, a first internal angle of the diamond is 10°-60°, the two edges of the first internal angle are used to cut the tendon sheath.

4. The Achilles tendon suture apparatus according to claim 1, wherein the spine portion has a taper, the apex angle of the taper is 60°-90°.

5. The Achilles tendon suture apparatus according to claim 1, wherein the front end of the tendon sheath cutter has a length of 1.2 cm-1.8 cm.

6. The Achilles tendon suture apparatus according to claim 1, wherein the guiding portion has a cone shape having an apex angle of 30°-45°.

7. An Achilles tendon suture apparatus comprising a first support and a second support, a distance regulating device, a first guiding sleeve and a second guiding sleeve, wherein:
   the first support and the second support both have a U type structure;
   the first support and the second support are connected by the distance regulating device;
   a first positioning hole is provided in an outer arm of the first support, a first guiding hole is provided in an inner arm of the first support;
   a second positioning hole is provided in an outer arm of the second support, a second guiding hole is provided in an inner arm of the second support;
   the centers of the first positioning hole, the first guiding hole, the second positioning hole and the second guiding hole are in a straight line,
   the first guiding sleeve has a rear end fixed in the outer arm of the first support by the first positioning hole, and a front end fitted into the first guiding hole;
   the second guiding sleeve has a rear end fixed in the outer arm of the second support by the second positioning hole, and a front end fitted into the second guiding hole;
   there are provided through holes in both of the first guiding sleeve and the second guiding sleeve for matching with Kirschner wire; further wherein:
   a front end of the inner arm of the first support bends in the direction of the second support, and a top portion of the front end of the inner arm of the first support is flexible;
   a front end of the inner arm of the second support bends in the direction of the first support, and a top portion of the front end of the inner arm of the second support is flexible.

8. The Achilles tendon suture apparatus according to claim 7, wherein the bending degree of the front end of the inner arm of the first support is the same as the bending degree of the front end of the inner arm of the second support.

9. The Achilles tendon suture apparatus according to claim 7, wherein the top of the front end of the inner arm of the first support has a thickness of 0.3 mm-1.0 mm, the top of the front end of the inner arm of the second support has a thickness of 0.3 mm-1.0 mm.

* * * * *